US010265222B2

(12) United States Patent
Okubo et al.

(10) Patent No.: US 10,265,222 B2
(45) Date of Patent: Apr. 23, 2019

(54) WEARING ARTICLE AND MANUFACTURING PROCESS FOR THE SAME

(71) Applicant: UNICHARM CORPORATION, Shikokuchuo-shi, Ehime (JP)

(72) Inventors: Tetsuo Okubo, Kanonji (JP); Tatsuya Hashimoto, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 704 days.

(21) Appl. No.: 14/772,782

(22) PCT Filed: Feb. 19, 2014

(86) PCT No.: PCT/JP2014/053845
§ 371 (c)(1),
(2) Date: Sep. 4, 2015

(87) PCT Pub. No.: WO2014/136572
PCT Pub. Date: Sep. 12, 2014

(65) Prior Publication Data
US 2016/0015574 A1    Jan. 21, 2016

(30) Foreign Application Priority Data

Mar. 8, 2013    (JP) ................................ 2013-047381

(51) Int. Cl.
*A61F 13/494* (2006.01)
*A61F 13/49* (2006.01)
*A61F 13/15* (2006.01)

(52) U.S. Cl.
CPC .. *A61F 13/49019* (2013.01); *A61F 13/15585* (2013.01); *A61F 13/15699* (2013.01);
(Continued)

(58) Field of Classification Search
CPC .......... A61F 13/15593; A61F 13/15699; A61F 13/49406; A61F 13/49413; A61F 13/4942;
(Continued)

(56) References Cited

U.S. PATENT DOCUMENTS 4,795,454 A * 1/1989 Dragoo ............. A61F 13/49009
604/378
6,248,097 B1 * 6/2001 Beitz ................. A61F 13/15593
604/358
(Continued)

FOREIGN PATENT DOCUMENTS

EP    1902694 A1    3/2008
JP    2002-209938 A    7/2002
(Continued)

OTHER PUBLICATIONS

International Search Report dated May 27, 2014 in International Application No. PCT/JP2014/053845.
Extended European Search Report in EP Application No. 14760595.0, dated Feb. 25, 2016.

*Primary Examiner* — Catharine L Anderson
(74) *Attorney, Agent, or Firm* — Hauptman Ham, LLP

(57) ABSTRACT

A wearing article includes a front waist panel, a rear waist panel and a crotch panel having an absorbent structure wherein respective inner end edges of the front and rear waist panels cooperate with both side edges of the crotch panel extending in a longitudinal direction to define peripheries of a pair of leg-openings. The crotch panel is provided with a pair of elasticized leg sheets joined to both side edges of the absorbent structure and extending in a longitudinal direction. Each of the elasticized leg sheets having a non-elasticized region adjacent to the absorbent structure and an elasticized region adjacent to the non-elasticized region so that the non-elasticized region rises along the associated side edge of the absorbent structure to the associated leg-opening (Continued)

and the elasticized region extends outward in a transverse direction of the wearing article so as to form the associated leg-opening.

12 Claims, 7 Drawing Sheets

(52) U.S. Cl.
CPC .. *A61F 13/15723* (2013.01); *A61F 13/15747* (2013.01); *A61F 13/15756* (2013.01); *A61F 13/15764* (2013.01); *A61F 13/49011* (2013.01); *A61F 13/49012* (2013.01); *A61F 13/49017* (2013.01); *A61F 13/4942* (2013.01); *A61F 2013/49022* (2013.01); *A61F 2013/49031* (2013.01); *A61F 2013/49092* (2013.01)

(58) Field of Classification Search
CPC .. A61F 2013/49088; A61F 2013/19092; A61F 2013/19095; A61F 2013/4948; A61F 2013/1539
See application file for complete search history.

(56) References Cited

U.S. PATENT DOCUMENTS

| | | | |
|---|---|---|---|
| 6,514,234 B2* | 2/2003 | Shimizu | A61F 13/49413 604/385.27 |
| 6,840,929 B2* | 1/2005 | Kurata | A61F 13/4753 604/385.28 |
| 8,075,543 B2* | 12/2011 | Okuda | A61F 13/15699 156/164 |
| 2012/0101466 A1* | 4/2012 | Oku | A61F 13/49406 604/385.16 |
| 2013/0079743 A1 | 3/2013 | Mukai et al. | |

FOREIGN PATENT DOCUMENTS

| | | |
|---|---|---|
| JP | 2002-522117 A | 7/2002 |
| JP | 2011-98052 A | 5/2011 |
| JP | 2011-110317 A | 6/2011 |
| JP | 2011-224134 A | 11/2011 |
| JP | 2013-226392 A | 11/2013 |

* cited by examiner

FIG.7
(a)
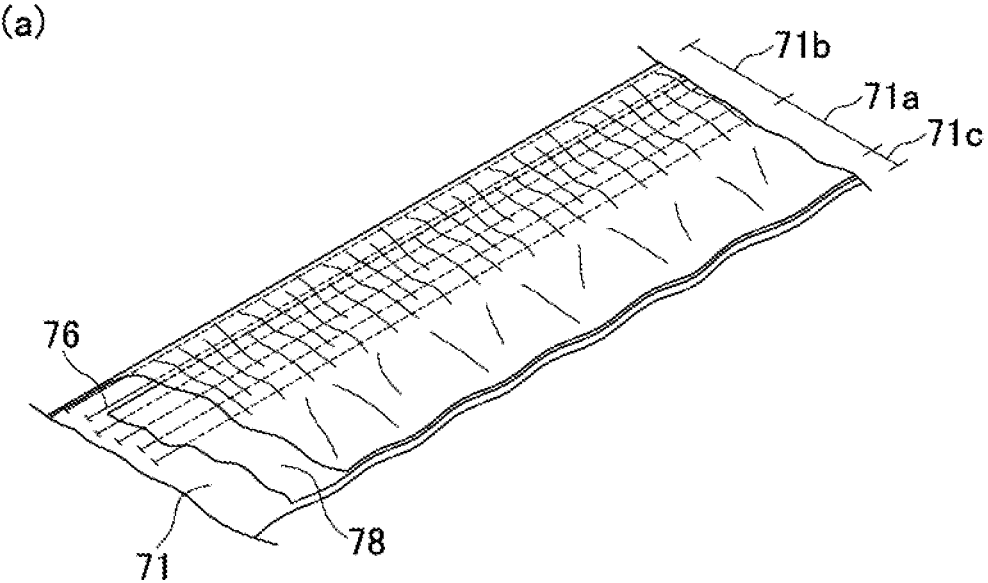
(b)
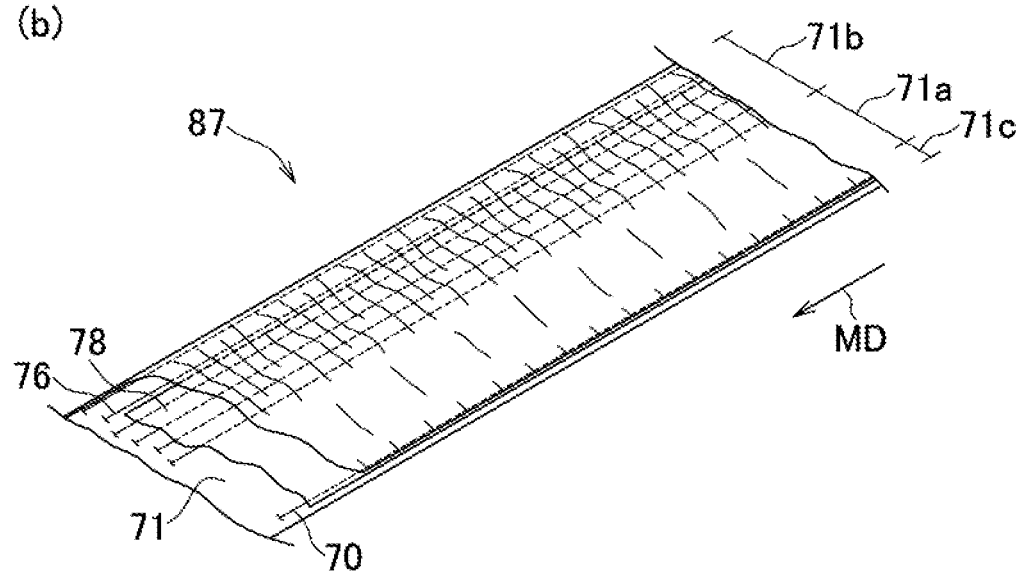

WEARING ARTICLE AND MANUFACTURING PROCESS FOR THE SAME

RELATED APPLICATIONS

The present application is a National Phase of International Application Number PCT/JP2014/053845, filed Feb. 19, 2014, which claims priority to Japanese Application Number 2013-047381, filed Mar. 8, 2013.

TECHNICAL FIELD

The present invention relates to wearing articles and manufacturing processes for the same and, more specifically, to wearing articles such as pull-on disposable diapers, disposable toilet-training pants and disposable pants for person with incontinence, each having waist elastic elements, and manufacturing processes for the same.

BACKGROUND

Conventionally, disposable wearing articles are known having waist elastic elements. For example, Patent Literature 1 discloses a disposable wearing article including an absorbent structure extending from a crotch region into front and rear waist regions and provided along both lateral sides with a plurality of strand- or string-like leg elastic elements and front and rear waist panels provided with a plurality of strand- or string-like waist elastic elements extending in a transverse direction.

CITATION LIST

Patent Literature

{PTL 1}: JP 2011-98052 A

SUMMARY

Technical Problem

In the disposable wearing article disclosed in Patent Literature 1, the elastic leg-cuffs including the leg elastic elements for the absorbent structure are fixed to the absorbent structure in the front waist region so as to be flattened inward in a transverse direction and fixed to the rear waist panel in the rear waist region so as to be flattened outward in the transverse direction. With such an arrangement, leakage of body exudates is restricted in the front waist region and, in the rear waist region, the elastic cuffs are sufficiently distanced from each other to ensure a sufficient width dimension of the absorbent structure to avoid a likelihood that the wearer' buttocks may be exposed to the outside.

However, the arrangement such that the elastic leg-cuffs are fixed to the absorbent structure in the rear waist region so as to be flattened outward in the transverse direction necessarily defines the crotch region to have a width dimension gradually broadening out from before backward. In consequence, when the front and rear waist regions are pulled up, the rear portion of the crotch region is not sufficiently pulled up and a gap may be left between the wearer's body and the crotch region through which body exudates may leak out from the article. Furthermore, if the crotch region is forcedly pulled up, the leg-openings may be tucked into the buttocks' cleavage and the buttocks may be partially exposed to the outside.

An object of the present invention is to improve the conventional disposable wearing articles and to provide wearing articles that the wearer's buttocks should not be exposed to the outside and assuring that the leg-openings are kept in close contact with the wearer's body at a desired fit to prevent body exudates from leaking out from the article and a manufacturing process for such wearing articles.

Solution to Problem

In order to solve the problem set forth above the present invention is directed to a wearing article having a longitudinal direction and a transverse direction, a skin-facing surface and a non-skin-facing surface. The article includes a front waist region, a rear waist region and a crotch region extending between the front and rear waist regions. The front and rear waist regions are joined to each other to form an annular elastic waist panel. A crotch panel is located in the crotch region so as to extend between the front and rear waist regions. An absorbent structure is located in a central area on the skin-facing surface of the crotch panel. The present invention is also directed to a manufacturing process for this wearing article.

According to the present invention features the article that a pair of elasticized leg sheets extending in the longitudinal direction are joined to respective side edge portions of a base layer as a constituent of the crotch panel. The elasticized leg sheets respectively include side sheets, a first elastic element and a second elastic element.

Each of the side sheets has a proximal side edge joined to the base layer and extending in the longitudinal direction and a distal side edge opposite to the proximal side edge and extending in the longitudinal direction. Each of side sheets are divided into a joint region extending along the proximal side edge, an elasticized region extending along the distal side edge and a non-elasticized region extending between the joint region and the elasticized region and provided with none of elastic elements. The second leg elastic elements are contractibly arranged under tension in the longitudinal direction along the joint region of the elasticized leg sheet and the first leg elastic elements are contractibly arranged under tension in the longitudinal direction in the elasticized region. Each of the elasticized leg sheets is joined to the base layer in such a state that the side sheet may be shrunk together with the first leg elastic elements and the second leg elastic elements but a stretch ratio of the first and second leg elastic elements may be maintained at a value larger than 1 and a number of gathers extending in parallel in the transverse direction may be formed in the joint region.

The present invention is also a manufacturing process for the wearing article according to the present invention includes the steps of continuously supplying first continuous elastic element and second continuous elastic element in a machine direction to and contractibly secured under tension to a first web for the side sheet and fed in the machine direction, then folding back the first web along a line preset for folding-back, joining the interior surface of the first web having been folded back so as to face itself and to interpose the first and second continuous elastic elements therebetween in a manner that the first continuous elastic element is arranged along the line preset for holding-back and the second continuous elastic element is arranged at a distance from the first continuous elastic element; shrinking the first web having been folded back in the machine direction so that respective stretch ratios of the first and second continuous elastic elements after having been shrunk are maintained at a value larger than 1; continuously feeding second webs for abase layer in the crotch panel in the machine direction and joining a joint region extending along the second continuous elastic element in the first web still being maintained in a shrunk state to the respective both side edge portions of the second web at once or sequentially; cutting a composite web composed of the first web joined to the both side edge portions of the second web in a direction orthogonal to the machine direction; and joining respective pieces of the composite web obtained in the step of cutting the composite web to a crotch region in a chassis manufactured in a separate manufacturing line and having the front waist region, the rear waist region and the crotch region extending between the front and rear waist regions.

Advantageous Effects of Invention

In the wearing article according to the present invention, each of the elasticized leg sheet has the joint region joined to the associated side edge portion of the base layer included by the crotch panel in the crotch region, the non-elasticized region including none of the elastic elements and the elasticized region in which the first leg elastic elements are contractibly arranged under tension. The elasticized leg sheet is shrunk together with the second leg elastic elements and the first leg elastic elements and secured to the base layer in the manner that both the second leg elastic elements and the first leg elastic elements maintain the stretch ratio larger than 1. As will be described in more detail, when the front and rear waist regions are joined to form the annular elastic waist panel, the non-elasticized regions of the respective elasticized leg sheets raise themselves along the side edges of the absorbent structure and the elasticized regions project outward in the transverse direction of the wearing article to for a pair of leg-openings. The leg-openings are provided with the first leg elastic elements having a stretch ratio larger than 1 and, with the wearing article put on the wearer's body, the leg-openings smoothly stretched and shrunk along the wearer's thighs at a desirable fit. In this way, it is possible not only to prevent body exudates from leaking sideways but also the leg-openings should not be tucked in the cleavage of the wearer's buttocks and the buttocks should be at least partially exposed to the outside.

In the wearing article according to the present invention, the second leg elastic elements are contractibly arranged under tension in the longitudinal direction along the joint region in which the base layer of the crotch panel and the elasticized leg sheet are joined to each other. According to the present invention, the elasticized leg sheet is joined in a shrunk state to the base layer. Considering this, if the second leg elastic elements are not present, the region in which the elasticized leg sheet and the base layer are joined to each other will be formed with large wrinkles. Consequently, when the elasticized leg sheet and the base layer are joined to each other with use of, for example, hot melt adhesive, a gap will be left between the elasticized let sheet and the base layer and this gap may cause leakage of body exudates from the both side edges of the absorbent structure. In contrast, when the second leg elastic elements are used, a number of gathers parallel extending in the transverse direction is formed in the region in which the elasticized leg sheet and the base layer are joined to each other but none of the large wrinkles will reach the joint region. In consequence, it is possible to join the elasticized leg sheet to the base layer without leaving any gap therebetween and it is possible to prevent leakage of body exudates further effectively.

The manufacturing process for the wearing article according to the present invention makes it possible to manufacture the wearing article such that the base layer as the constituent of the crotch panel is provided with a pair of the elasticized leg sheets joined under tension to the both side edge portions of the base layer, the joint regions in which the base layer and the elasticized leg sheets are joined to each other are formed with a number of gathers parallel extending in the transverse direction, and the second leg sheets are provided to prevent any gap from being left between the elasticized leg sheet and the base layer. In this way, according to the manufacturing process of the wearing article with the article put on the wearer's body, the wearer's buttocks should not be exposed to the outside and ensuring that the leg-openings are kept in close contact with the wearer' body at the desired fit to prevent body exudates from leaking out from the article.

BRIEF DESCRIPTION OF DRAWINGS

The drawings illustrate specific embodiments of the present invention including optional and preferred embodiments as well as essential features of the invention.

FIG. 7 is a schematic diagram illustrating part of sheet web having been retracted in a processing step.

DESCRIPTION OF EMBODIMENTS

Figure 1:
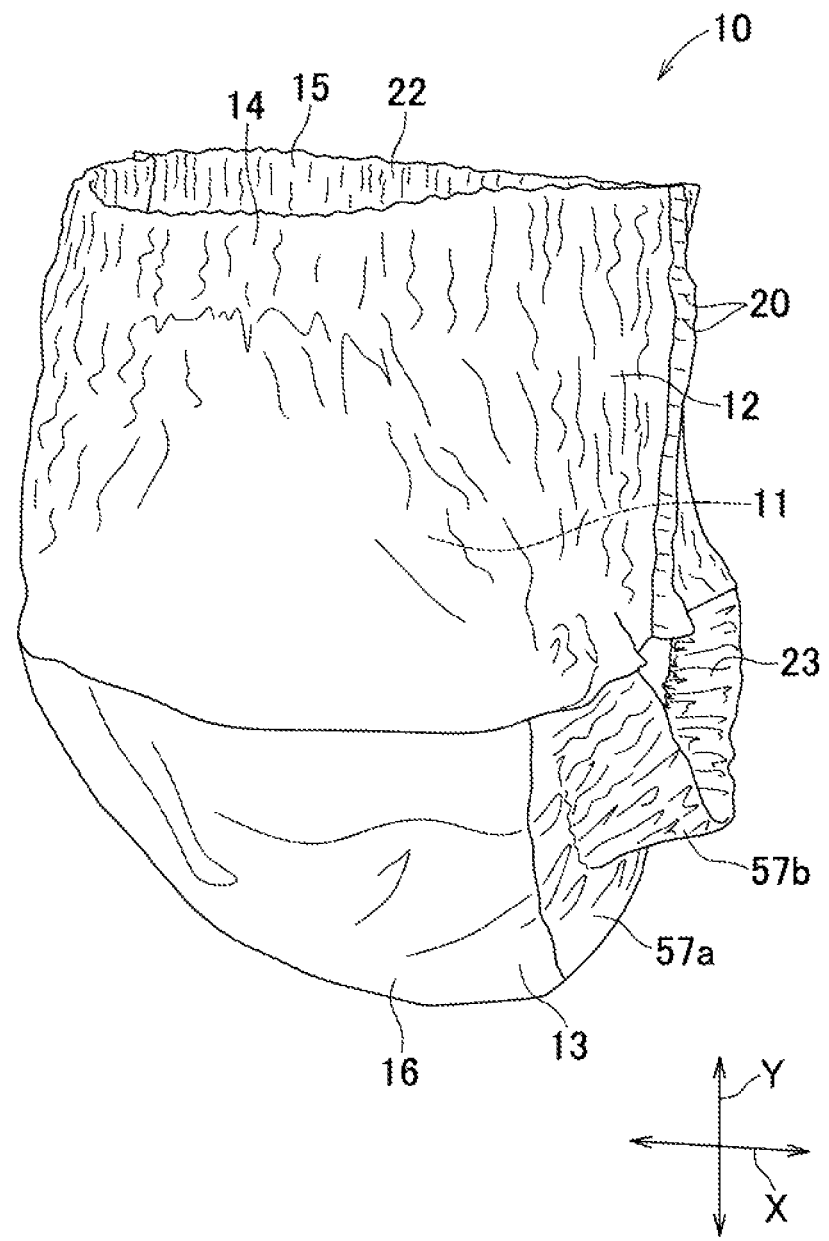
FIG. 1 is a perspective view illustrating a disposable diaper as an example of a wearing article according to the present invention.
Figure 2:
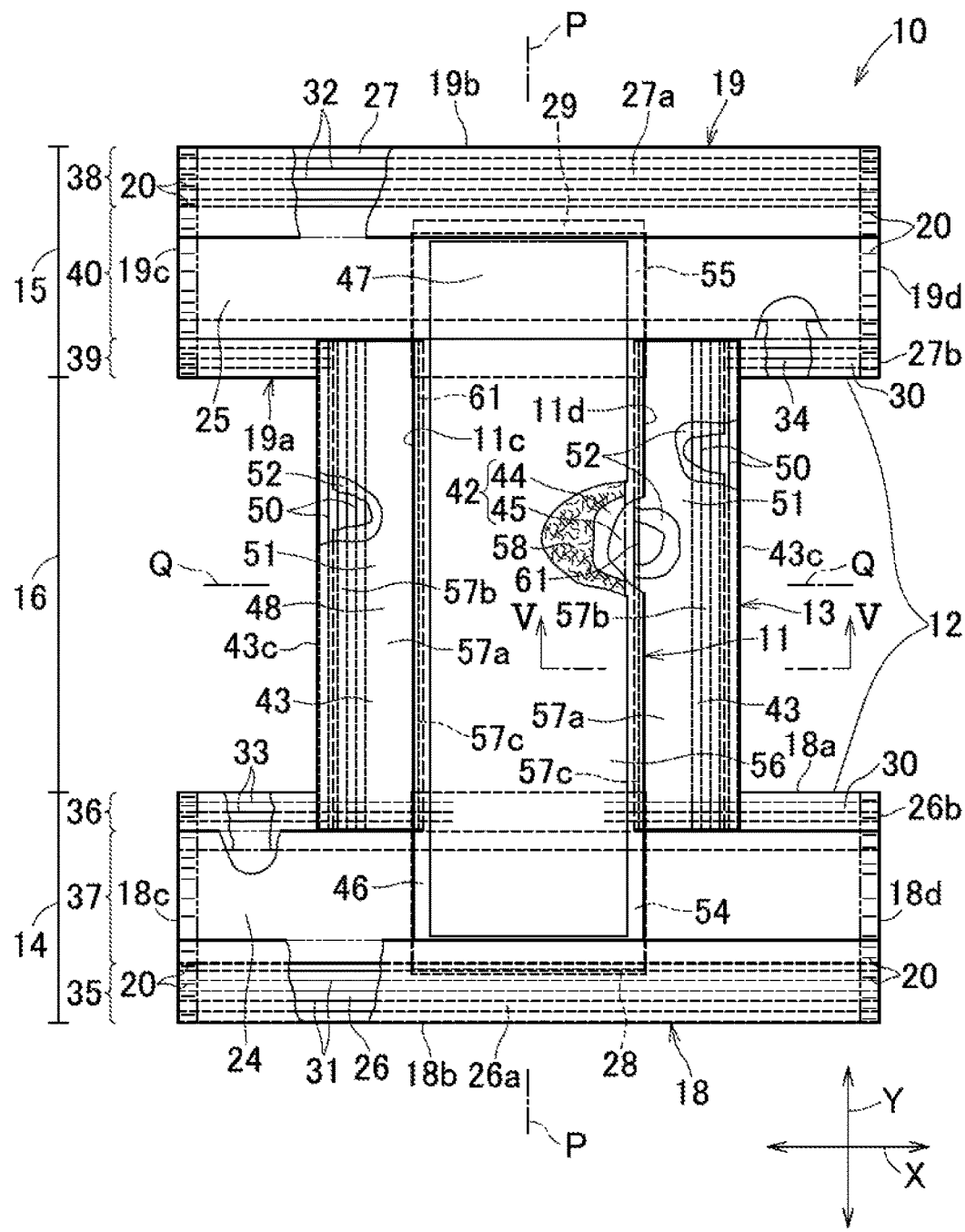
FIG. 2 is a partially cutaway plan view of the diaper developed in a flat state.
Figure 3:
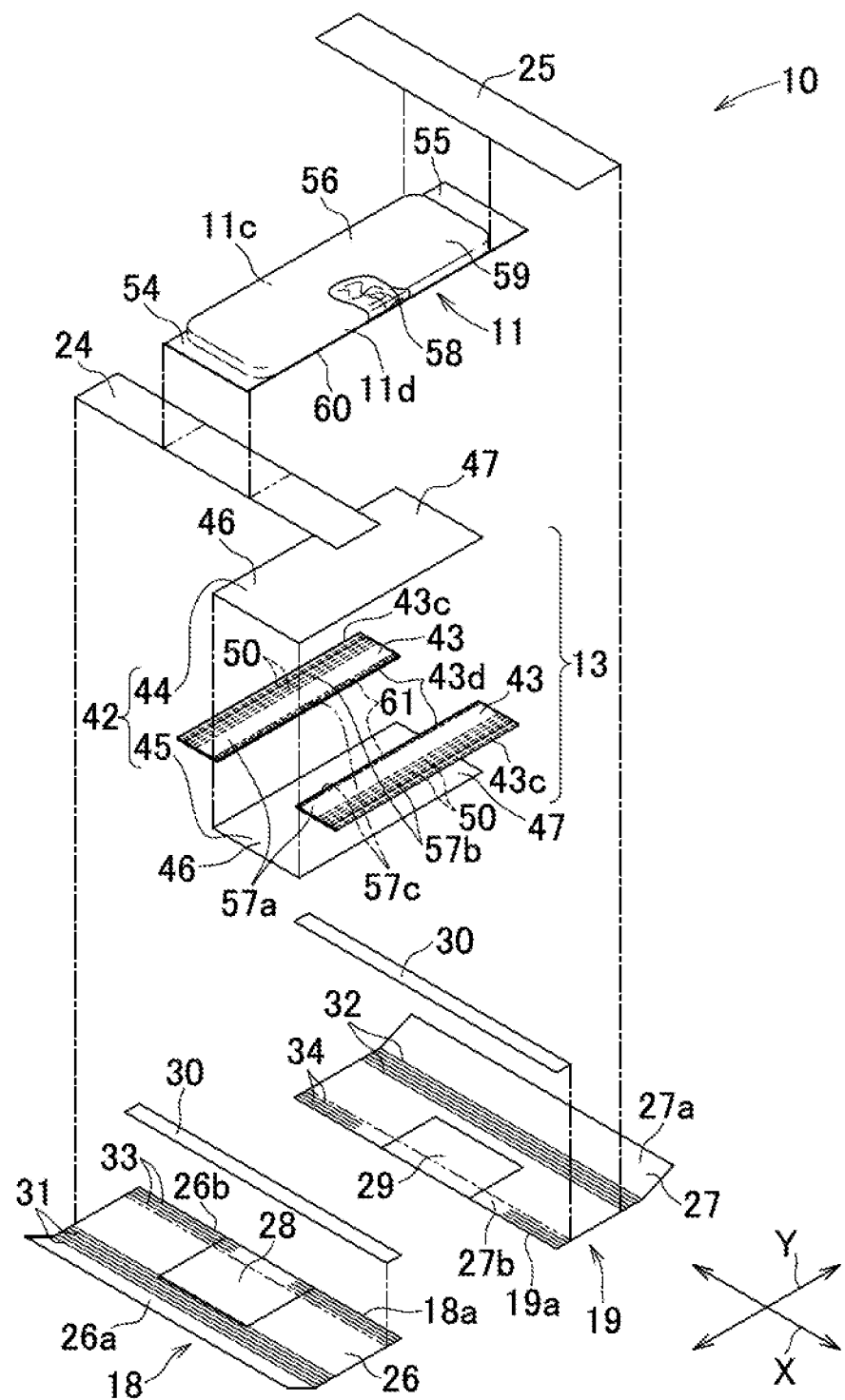
FIG. 3 is an exploded perspective view of the diaper.
Figure 4:
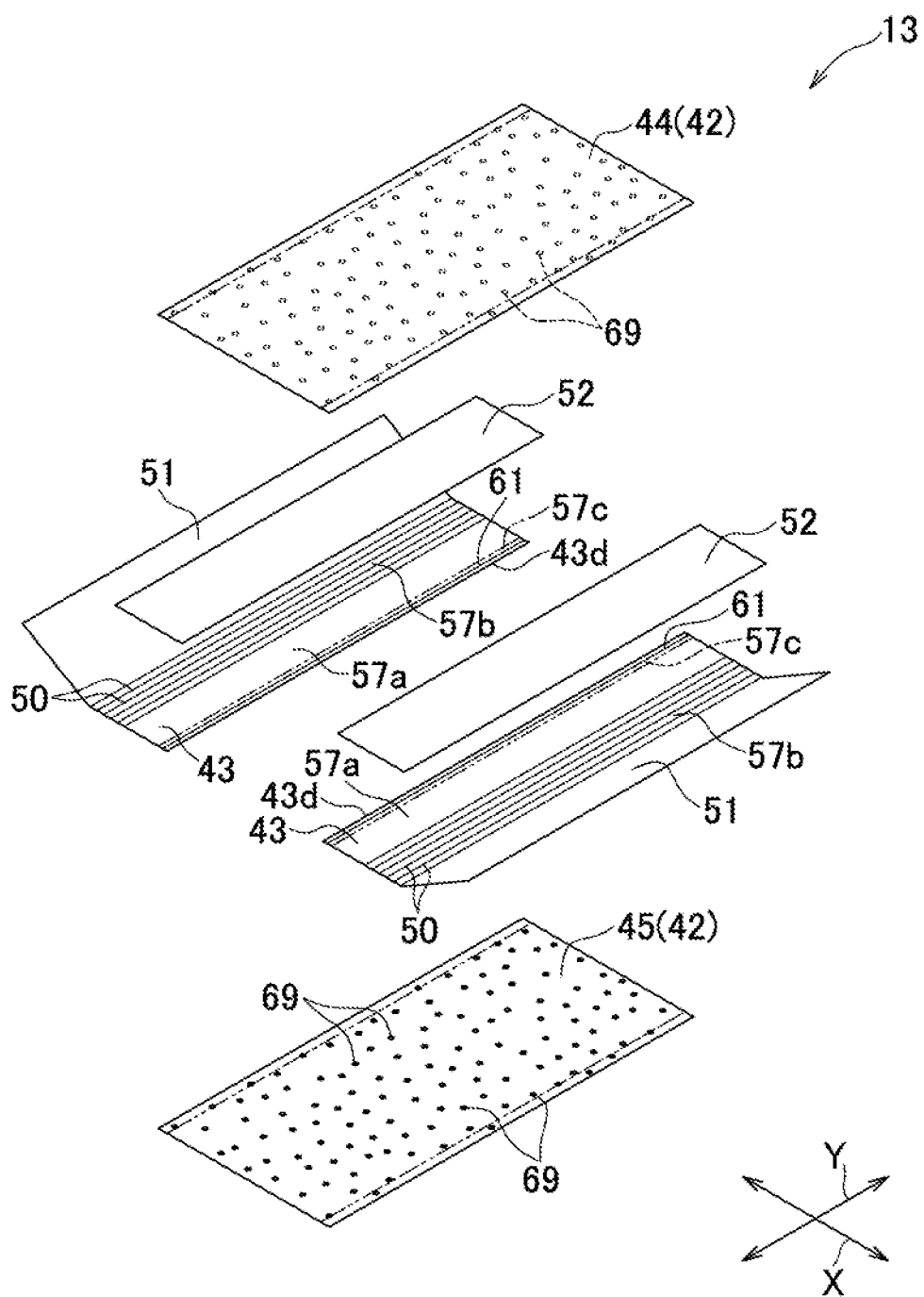
FIG. 4 is an exploded perspective view of a crotch panel.
Figure 5:
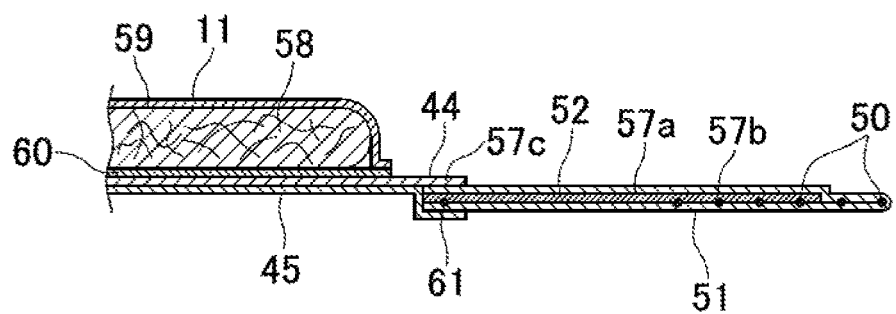
FIG. 5 is a schematic sectional view taken along line V-V in FIG. 2.

A wearing article according to the present invention will be described hereunder on the basis of a pull-on disposable diaper 10 as a typical example thereof. Referring to FIGS. 1 through 3, the disposable diaper 10 has a longitudinal direction Y, a transverse direction X, a skin-facing surface facing the wearer's skin, a non-skin-facing surface opposed to the skin-contact surface and includes a front waist region 14, a rear waist region 15 and a crotch region 16 extending between the front and rear waist regions 14, 15. The diaper 10 includes, as a basic structure, an annular elastic waist panel 12 circumferentially extending around the wearer's waist, a crotch panel 13 and an absorbent structure 11 located on the skin-facing surface of the crotch panel 13.

The elastic waist panel 12 functions as an elastic belt to hold the absorbent structure 11 in a crotch region of the wearer and includes a front waist panel 18 defining the front waist region 14 and a rear waist panel 19 defining the rear waist region 15. The front waist panel 18 has a laterally longer rectangular shape contoured by an inner end edge 18a and an outer end edge 18b both extending in the transverse direction X and both side edges 18c, 18d extending in the longitudinal direction Y between the inner and outer end edges 18a, 18b. The rear waist panel 19 also has a laterally longer rectangular shape defined by an inner end edge 19a and an outer end edge 19b both extending in the transverse direction X and both side edges 19c, 19d extending in the longitudinal direction Y between the inner and outer end edges 19a, 19b. The both side edges 18c, 18d of the front waist panel 18 are joined to the corresponding both side edges 19c, 19d of the rear waist panel 19 at seams continually made in the longitudinal direction with use of well known technique, for example, thermal fusion bonding technique such as hot embossing/debossing or ultrasonic processing. In this way, the annular elastic waist panel 12 is formed and a waist-opening 22 is defined by the outer end edges 18b, 19b. In this regard, the respective inner end edges 18a, 19a of the front and rear waist panels 18, 19 cooperate with elasticized leg-sheets 43 arranged in the crotch panel 13 to define a pair of leg-openings 23.

The front and rear waist panels 18, 19 respectively include main panels 26, 27 and auxiliary panels 24, 25. The auxiliary panels 24, 25 respectively have width dimensions in the longitudinal direction Y smaller than those of the main panels 26, 27 and located on the skin-facing surfaces of the main panels 26, 27 so as to be rather close to the inner end edges 18a, 19a thereof.

As material for the main panels 26, 27, SMS (spunbonded/meltblown/spunbonded) fibrous nonwoven fabrics, spunbonded nonwoven fabrics, air-through nonwoven fabrics, plastic films or laminate sheets formed of any one of various types of fibrous nonwoven fabrics described just above and plastic sheets, each having a mass per unit area in a range of about 15 to about 30 g/m2, may be used. The auxiliary panels 24, 25 are joined to the main panels 26, 27, respectively, with hot melt adhesive distributed to the interior surface of at least one of the respective main and auxiliary panels facing each other or with use of well known thermal fusion bonding techniques.

As material for the auxiliary panels 24, 25, various types of well known elastic fibrous nonwoven fabrics such as a spunbonded fibrous nonwoven fabric, a meltblown fibrous nonwoven fabric, a heat-roll fibrous nonwoven fabric, an SMS fibrous nonwoven fabric, an air-laid fibrous nonwoven fabric or air-through fibrous nonwoven fabric may be used independently or in combination. The elastic nonwoven fabrics may be formed from, for example, a polyethylene-based or polyurethane-based elastomer resin or polyethylene, polyester-based or an acrylic thermoplastic resin. While it is possible to use inelastic fibrous nonwoven fabrics as material for the auxiliary panels 24, 25, at least the auxiliary panel 24 is preferably formed of elastic fibrous nonwoven fabrics.

Referring to FIGS. 2 and 3, graphic patches 28, 29 formed from plastic materials and having graphics (not shown) or the like displayed thereon so as to be visually recognizable through the non-skin-facing surface from the outside are interposed between the auxiliary panels 24, 25 and the main panels 26, 27 in central regions of the front and rear waist regions 14, 15, respectively, as viewed in the transverse direction X. In the front and rear waist panels 18, 19, portions of the main panels 26, 27 extending outward in the longitudinal direction Y beyond the respective outer end edges of the auxiliary panels 24, 25 are folded back inward and, within respective folded-back portions 26a, 27a, a plurality of strand- or string-like first and second waist-elastics 31, 32 are contractibly secured under tension, for example, with hot melt adhesive. Meanwhile, securing sheet strips 30 formed of fibrous nonwoven fabrics are arranged on respective inner end portions 26b, 27b of the main panels 26, 27 and strand- or string-like third and fourth waist-elastic elements 33, 34 are interposed and contractibly secured under tension, for example, with hot melt adhesive between the securing sheet strips 30 and the inner end portions 26b, 27b, respectively.

The front waist panel 14 has an outer end sub-region 35 in which the first waist elastic elements 31 are arranged, an inner end sub-region 36 in which the third waist elastic elements 33 are arranged and an intermediate sub-region 37 defined between the outer and inner end sub-regions 35, 36. The rear waist region 15 has an outer end sub-region 38 in which the second waist elastic elements 32 are arranged, an inner end sub-region 39 in which the fourth waist elastic elements 34 are arranged and an intermediate sub-region 40 defined between the outer and inner end sub-regions 38, 39. In the respective intermediate sub-regions 37, 40 including none of the waist elastic elements, the elastic auxiliary panels 24, 25 are respectively arranged. Such arrangement in the diaper put on the wearer's body ensures that the respective outer end sub-regions 35, 38 and the respective inner end sub-regions 36, 39 of the front and rear waist regions are stably kept in close contact with the wearer's body at desirable degree of fit under contractile force of the respective waist elastics 31, 32, 33, 34 and the respective intermediate sub-regions 37, 40 also are kept in close contact with the wearer's body at desirable degree of fit under contractile force of the auxiliary panels 24, 25. In consequence, there is the diaper 10 should not be displaced to an extent causing leakage of body exudates.

The crotch panel 13 located in the crotch region 16 includes a base layer 42 located in a central region in the transverse direction X and a pair of the elasticized leg sheets 43 joined to the skin-facing surface of the base layer 42 along both lateral portions thereof. The base layer 42 is formed of an interior sheet 44 located on the side of the skin-facing surface and an exterior sheet 45 located on the side of the non-skin-facing surface. As material for these interior and exterior sheets 44, 45, various kinds of fibrous nonwoven fabrics or moisture-permeable plastic films both of well known art may be used. As will be described later in more details, the interior sheet 44 is preferably formed of liquid-impermeable/moisture-permeable plastic films considering that the interior sheet 44 is located to face the absorbent structure 11 and the exterior sheet 45 is preferably formed of fibrous nonwoven fabrics having a texture superior to that of plastic films considering that the exterior sheet 45 partially defines the exterior surface of the diaper 10.

The crotch panel 13 has front and rear end sub-regions 46, 47 and an intermediate sub-region. The front and rear end sub-regions 46, 47 are fixed to the respective skin-facing surfaces of the front and rear waist panels 18, 19 adjacent to the respective inner end edges 18a, 19a of the front and rear waist panels 18, 19 by joining regions arranged on the non-skin-facing surfaces of the front and rear end sub-regions 46, 47, respectively, and coated with, for example, hot melt adhesive. As the first through fourth waist elastic elements 31, 32, 33, 34, elastic materials having a fineness in a range of 480 to 940 dtex may be used under tension at stretch ratio in a range of 2.0 to 3.5.

The absorbent structure 11 has a longitudinally longer pad shape and includes front and rear end portions 54, 55, an intermediate portion 56, an absorbent core 56 extending in the longitudinal direction Y at least in the crotch region 16, a body side liner 59 located on the side of the skin-facing surface of the absorbent core 58 and an exterior cover 60 located on the side of the non-sin-facing surface of the absorbent core 58. The almost entire non-skin-facing surface of the absorbent structure 11 is coated with hot melt adhesive in well known patterns. The front and rear end portions 54, 55 are respectively fixed to the skin-facing surfaces of the front and rear waist panels 18, 19 with the hot melt adhesive and the intermediate portion 56 also is fixed to the skin-facing surface of the crotch panel 13 with the hot melt adhesive. As illustrated in FIG. 3, the front end portion 54 of the absorbent structure 11 is fixed to the skin-facing surface of the auxiliary panel 24 of the front waist panel 18 and the rear end portion 55 is fixed to the skin-facing surface of the main panel 27 in a state interposed between these auxiliary panel 25 of the rear waist panel 19 and the main panel 27. With the front end portion 54 of the absorbent structure 11 being fixed to the skin-facing surface of the auxiliary panel 24 in this manner, the front end portion 54 of the absorbent structure 11 will be elastically pressed to be kept in contact with the wearer's body so long as the auxiliary panel 24 has an elasticity and whereby it will be possible to prevent body exudates from migrating and leaking out from the diaper. Meanwhile, the arrangement that the rear end portion 55 is interposed between the auxiliary panel 25 and the main panel 27 and fixed in this state makes it possible to prevent body exudates may be in direct contact with the wearer's skin.

The absorbent core 58 has a mass per unit area in a range of about 400 to about 600 g/m2 and includes a core formed of wood fluff pulp, superabsorbent polymer particles (SAP) and optionally thermal fusion bonding staple fibers and liquid-permeable tissue paper or fibrous nonwoven fabrics covering the core. As material for the body side liner 59, various types of fibrous nonwoven fabrics of well known art such as a liquid-permeable spunbonded nonwoven fabrics and an SMS nonwoven fabrics each having a mass per unit area in a range of about 10 to about 30 g/m2 may be used. As material for the exterior cover 60, for example, liquid-impermeable spunbonded nonwoven fabrics, SMS nonwoven fabrics, plastic sheets or laminate sheet of fibrous nonwoven fabrics and fibrous nonwoven fabrics each having a mass per unit area in a range of about 10 to about 30 g/m2 may be used. Though not illustrated, it is also possible to employ an alternative arrangement such that both the body side liner 59 and the external cover 60 extend outward in the transverse direction X beyond the both side edges of the absorbent core 58 and a plurality of strand- or string-like elastics are contractibly attached to these portions extending beyond the side edges to define a pair of leg-cuffs adapted to rise toward the wearer's crotch region during use of the diaper.

Referring to FIGS. 2 through 5, each of the elasticized leg sheets 43 has a generally rectangular shape and includes a side sheet 51 having a proximal side edge 43d joined to the base layer 42 and extending in the longitudinal direction Y and a distal edge 43c facing the proximal side edge 43d and extending in the longitudinal direction Y, first leg elastic elements 50 and second leg elastic elements 61 respectively secured to the side sheet 51 and an elongate reinforcing sheet 52. The elasticized leg sheet 43 includes a joint region 57c extending along the proximal edge 43d, an elasticized region 57b extending along the distal edge 43c and a non-elasticized region 57a extending between the joint region 57c and the elasticized region 57b. A dimension of the non-elasticized region 57a is typically in a range of 10 mm to 25 mm, a dimension of the elasticized region 57b is typically in a range of 20 mm to 35 mm and a dimension of the joint region 57c is typically in a range of 2 mm to 5 mm.

The single second leg elastic elements 61 extends in the longitudinal direction Y under tension along the joint region 57c of the elasticized leg sheet 43 and, in the elasticized region 57b, a plurality of the first leg elastic elements 50 extend in the longitudinal direction Y under tension. According to this embodiment, the second leg elastic elements 61 is arranged in the joint region 57c. The first leg elastic elements 50 and the second leg elastic elements 61 are secured together with the reinforcing sheet 52 to the interior side of the doubled-up side sheet 51 with hot melt adhesive in a manner that the first leg elastic elements 50 are located in the vicinity of the line preset for folding-back and the second leg elastic elements 61 is located in the vicinity of the opened end edge of the doubled-up side sheet 51.

The side sheets 51 define the leg-opening 23 of the diaper 10 and respectively formed of generally rectangular fibrous nonwoven fabrics sheets. The reinforcing sheets 52 are respectively formed of generally rectangular plastic sheets and the first leg elastic elements 50 and the second leg elastic elements 61 are respectively arranged on the interior surfaces thereof. As the first leg elastic elements 50 and the second leg elastic elements 61, for example, elastic elements having a fineness in a range of 310 to 780 dtex may be used at stretch ratio in a range of 2.0 to 4.0 but not limited thereto. The first leg elastic elements 50 and the second leg elastic elements 61 may be contractibly secured under tension to the respective side sheets 51, respectively, for example, with hot melt adhesive distributed onto the respective side sheets 51 in well known a pattern such as spiral- or a dotted-pattern.

Preferably, the stretch ratio of a plurality of the first leg elastic elements 50 is uniformly set or the stretch ratio of the one or more first leg elastic elements 50 arranged in the vicinity of a boundary between the elasticized region 57b and the non-elasticized region 57a is set to be higher than that of the remaining first leg elastic elements 50. By setting the stretch ratio of the first leg elastic elements 50 in this manner, it is ensured that the first leg elastic elements 50 arranged in the vicinity of the respective boundaries between the elasticized regions 57b and the non-elasticized regions 57a of the diaper 10 put on the wearer's body contract and, in consequence, the respective non-elasticized regions 57a rise along the respective side edges 11c, 11d. Furthermore, the remaining first leg elastics 50 contract at the same degree as the first leg elastic elements 50 located in the vicinity of the respective boundaries between the elasticized regions 57b and the non-elasticized regions 57a and consequently the elasticized regions 57b respectively take shapes projecting outward in the transverse direction X to form the pair of leg-openings 23. With the diaper 10 put on the wearer's body, the leg-openings 23 are sufficiently stretched along the wearer's thighs at desirable fit. In this way, body exudates should not leak sideways and, in addition, the leg-openings should not be tucked down between the wearer's buttocks and the buttocks should not be partially exposed to the outside.

The elasticized leg sheets 43 cooperate with the associated second and first leg elastic elements 61, 50 to cause the side sheets 51 to contract and are joined to both side edges of the respective base layers 42 in a state that the dimension in the longitudinal direction Y is shorter than the dimension of the side sheet 51 before the second leg elastic elements 61 and the first leg elastic elements 50 are secured and the stretch ratios of the second leg elastic elements 61 and the first leg elastic elements 50 is larger than 1. According to the present embodiment, entire interior surfaces of the interior sheet 44 and the exterior sheet 45 are coated with, for example, hot melt adhesive 69 so that the joined regions 57c of the respective elasticized leg sheets 43 are joined in a state interposed between the interior sheet 44 and the exterior sheet 45.

When the elasticized leg sheets are let contract to be attached to the base layer 42, regular and fine wrinkles (designated thereafter as "gathers") are formed in the elasticized regions 57b of the side sheets 51 owing to contraction of the first leg elastic elements 50. Meanwhile, in the non-elasticized regions 57*a* adjacent to the respective elasticized regions 57*b* including none of the elastic elements, the side sheets 51 undulate, in other words, wrinkles arranged at intervals larger than those of gathers are formed in the non-elasticized regions 57*a*. Assuming that the second leg elastic elements 61 is not present along each of the joint regions 57*c*, such wrinkles arranged at large intervals will reach this joint region 57*c* and consequently gaps will be left between the elasticized leg sheet 43 and the base layer 42 when the elasticized leg sheet 43 is joined to the base layer 42 with, for example, hot melt adhesive, body exudates may leak along the side edges of the absorbent structure 11.

However, when the second leg elastic elements 61 is arranged along each of the joint region 57*c*, the fine gathers are formed due to contraction of this second leg elastic elements 61 and the large wrinkles should not reach the respective joint regions 57*c*. In other words, the large wrinkles are interrupted by the respective second leg elastic elements 61. In this way, it is possible to join the joint regions 57*c* free from any large wrinkles to the base layer 42 with, for example, hot melt adhesive so that the elasticized leg sheet 43 may be joined to the base layer 42 without leaving any gap therebetween. Thus, leakage of body exudates out from the article is effectively prevented. In the elasticized leg sheets 43 joined to the both lateral sides of the base layer 42, a number of gathers are formed along the respective second leg elastic elements 61 and the respective first leg elastic elements 50 and, between the respective second leg elastic elements 61 and the respective first leg elastic elements 50, a plurality of wrinkles arranged at intervals larger than the intervals of the gathers formed by the respective second leg elastic elements 61 and the respective first leg elastic elements 50.

In the longitudinal direction Y of the elasticized leg sheet 43, a ratio of a dimension of the elasticized leg sheet 43 before contraction versus a dimension thereof after contraction (i.e., dimension before contraction/dimension after contraction) is preferably in a range of 1.05 to 1.5. So far as the dimension ratio of the elasticized leg sheet 43 before and after contraction is within this range, it is ensured that the respective elasticized leg sheets 43 of the article put on the wearer's body are stretched around the wearer's thighs and stably kept in close contact with at a degree of desired fit and a degree of contractile force required for leakage prevention is fulfilled. If the dimension ratio before and after contraction of the elasticized leg sheet 43 is larger than 1.5, the stretch ratio of the first leg elastic elements 50 after the elasticized leg sheet 43 has been joined to the base layer 42 will excessively decrease to contract closely around the wearer's thighs. If the dimension ratio before and after contraction of the elasticized leg sheet 43 is less than 1.05, an extensible length of the elasticized leg sheet 43 when the article is put on the wearer's body will be insufficient to be stably kept in close contact around the wearer's thighs at desired fit.

Adjustment of the dimension ratio before and after contraction of the elasticized leg sheet 43 at the moment of joining the elasticized sheet 43 to the base layer 42 may be easily achieved by controlling the length of the side sheet 51 after contraction relative to the length of the side sheet 51 before contraction in the step of causing the side sheet 51 to contract together with the first leg elastic elements 50 and the second leg elastic elements 61 after the first leg elastic elements 50 and the second leg elastic elements 61 have been secured under tension to a flat sheet material defining the side sheet 51.

A dimension ratio before and after contraction of the elasticized leg sheet 43 within the diaper 10 in the form of a finished product may be measured with use of a test piece prepared by cutting the elasticized leg sheet 43 joined to the side edge portion of the base layer 42 in the crotch region 16 together with the base layer 42. Specifically, a test piece inclusive of the joint region 57*c* having an arbitrary length (e.g., 10 cm) in the longitudinal direction Y is cut out from the base layer 42 and the elasticized leg sheet 43 lying in the region adjacent to the joint region 57*c* extending in the longitudinal direction in the crotch region 16 of the diaper 10. This test piece is prepared in a rectangular shape. Then, the sheet materials respectively forming the base layer 42 and the elasticized sheet 45 (i.e., the interior and exterior sheet 44, 45 and the side sheet 51) in the region adjacent to the joint region 57*c* are cut out so as to have a given width (e.g., 5 mm) and dimensions in the longitudinal direction Y of these pieces are measured. Since the elasticized leg sheet 43 has been joined in a state of contraction to the side edge portion of the base layer 42, a dimension of the sheet material forming the elasticized leg sheet 43 (i.e., the side sheet 51) is larger than that of the sheet material forming the base layer 42 (i.e., the interior sheet 44 and the exterior sheet 45). In view of this, a dimension ratio before and after contraction of the elasticized leg sheet 43 may be calculated from the dimension ratio between the sheet material forming the elasticized leg sheet 43 and the sheet material forming the base layer 42. While it is unnecessary to describe, the test piece is prepared so that the cut out sheet materials forming the base layer 42 and the elasticized leg sheet 43 include none of the first leg elastic elements 50 and the second leg elastic elements 61.

When the first leg elastic elements 50 and the second leg elastic elements 61 are secured to each of the side sheets 51, the stretch ratio of the first leg elastic elements 50 is preferably set so as to be higher than the stretch ratio of the second leg elastic elements 61. The respective stretch ratios may be set to ensure that the number of gathers formed along the second leg elastic elements 61 is fewer than the number of gathers generated along the first leg elastic elements 50 and, in consequence, the joint regions 57*c* become relatively flat. Consequently, substantially no gap is formed when the elasticized leg sheet 43 is joined to the base layer 42 and it is assured that leakage of body exudates is effectively prevented.

The elasticized region 57*b* of the elasticized leg sheet 43 is preferably subjected to a pleating treatment. The pleating treatment may be put into effect by guiding the elasticized region 57*b* to pass between a pair of mating toothed rollers. Since the elasticized regions 57*b* of the elasticized leg sheet 43 are to be stretched in the respective leg-openings 23 around the wearer's thighs, the elasticized regions 57*b* may be subjected to the pleating treatment to improve the texture of the leg-openings.

While the present invention has been exemplarily described hereinabove on the basis of the embodiment in which the diaper 10 is formed by the crotch panel 13, the front waist panel 18 and the rear waist panel 19 each having a rectangular shape, the present invention is not limited to such embodiment and may be embodied regardless of shapes of the front waist region 14, the rear waist region 15 and the crotch region 16. Further, while the present invention has been described above on the basis of the embodiment in which the second leg elastic elements 61 is arranged in the joint region 57*c*, it is also possible to arrange the second leg elastic elements 61 so as to be adjacent to the joint region 57c unless the large wrinkles extend to the joint region 57c.

Figure 6:
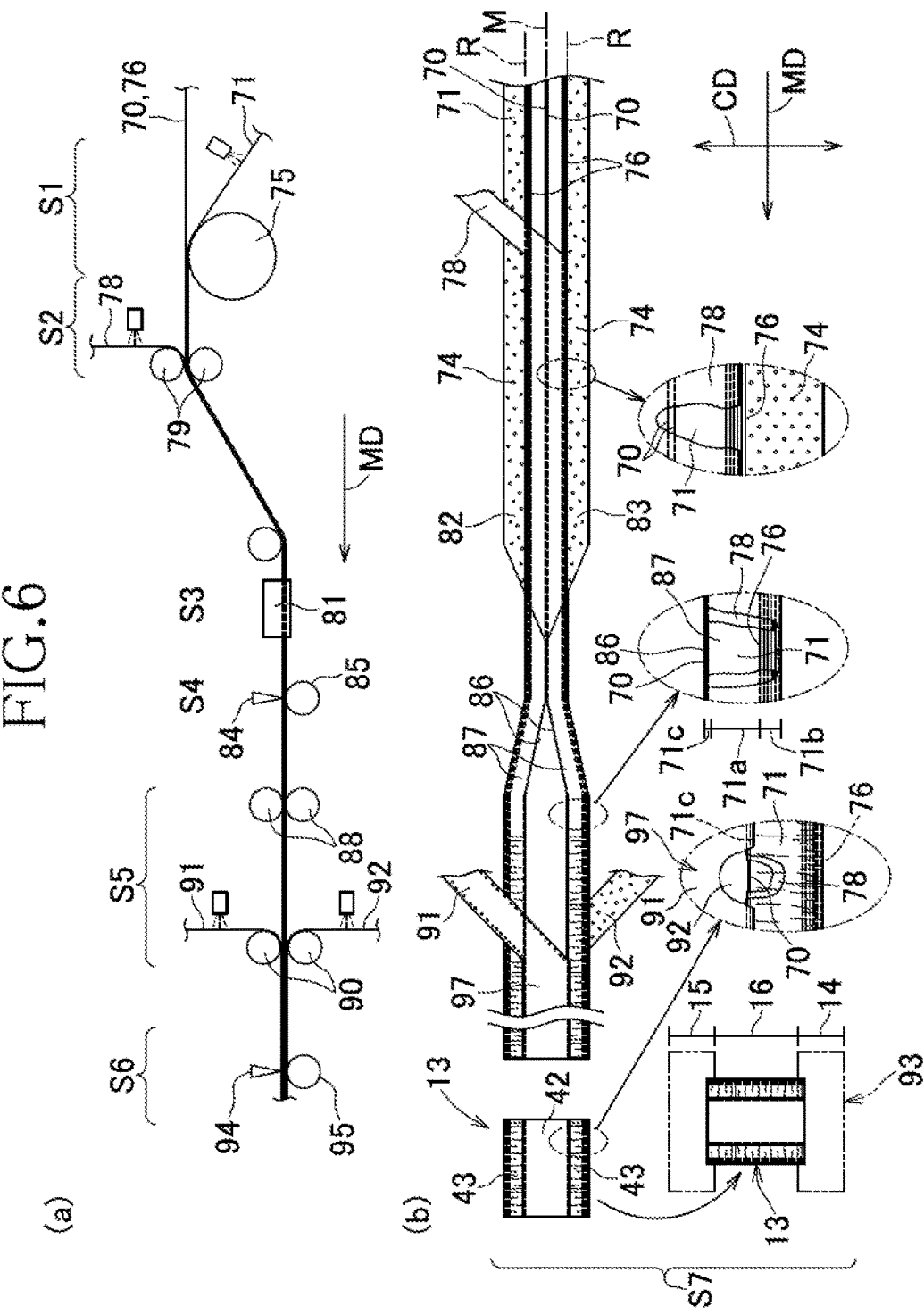
FIG. 6 is a schematic diagram illustrating a manufacturing process for the diaper including elasticized leg-sheets.

Referring now to FIGS. 6 and 7, a manufacturing process for the diaper 10 according to the present invention including the elasticized leg sheets 43 will be described on the basis of an embodiment. To facilitate understanding of the present invention, the process according to the present embodiment will be described, as illustrated in FIG. 6 (*a*), step by step along a machine direction MD, specifically in the order of an attaching step S1, a covering step S2, a folding step S3, a first cutting step S4, a retracting/joining step S5, a second cutting step S6 and an assembling step S7. FIG. 6 (*b*) is a schematic diagram illustrating states of web in the respective steps in FIG. 6 (*a*) in a plan view. In this regard, a crossing direction CD is the direction being orthogonal to the machine direction MD and various kinds of web and elastic elements used to producing the elasticized leg sheets 43 are conveyed along the machine direction MD.

<Attaching Step S1>

In this step, a second continuous elastic element 70 for the second leg elastic elements 61 and a plurality of first continuous elastic elements 76 for the first leg elastic elements 50 are continuously fed along respective courses distanced from each other in the cross direction CD to a first web 71 for the side sheets 51 and these second and first continuous elastic elements 70, 76 are secured under tension to the first web 71. According to the present embodiment, a pair of the second continuous elastic elements 70 and a pair of the first continuous elastic elements 76 are fed symmetrically around an imaginary center line M bisecting a dimension of the first web 71 in the cross direction CD and a pair of the second continuous elastic elements 70 is secured to both lateral portions of the first web 71 defined symmetrically about the imaginary center line M so as to be adjacent to the imaginary center line M. A distance between the imaginary center line M and the respective second continuous elastic elements 70 may be, for example, in a range of 2 to 5 mm. Between the imaginary center line M and a pair of lines R preset for folding-back, the first continuous elastic elements 76 are secured to the first web 71 in a manner that the respective first continuous elastic elements 76 may be distanced from the second continuous elastic element 70. The first continuous elastic elements 76 are preferably arranged so as to be adjacent to the respective lines R preset for folding-back. A distance between the second continuous elastic element 70 and the first continuous elastic elements 76 is typically in a range of 10 mm to 25 mm.

In this step, portions of the first web 71 to which the second continuous elastic elements 70 and the first continuous elastic elements 76 are secured and portions of the first web 71 defined between the line R preset for folding-back and side edges of the first web 71 are previously coated with hot melt adhesive 74 and the first web 71 coated with hot melt adhesive is supplied to a rotary drum 75. In parallel with this, the second continuous elastic element 70 and the first continuous elastic element 76 are fed, under predetermined stretch ratios, together with the first web 71 so that the second continuous elastic element 70 and the first continuous elastic element 76 may be secured to the first web 71. The respective stretch ratio values of the second continuous elastic element 70 and the first continuous elastic element 76 may be controlled by adjusting feed rates of the respective elements.

<Covering Step S2>

In this step, the second and first continuous elastic elements 70, 76 are covered with a third web 78 for the reinforcing sheet 52. Specifically, the third web 78 previously coated with hot melt adhesive on a surface to which the second and first continuous elastic elements 70, 76 are to be secured and the first web 71 to which the second and first continuous elastic elements 70, 76 have been secured are fed to pass through between a pair of nip rollers 79. The third web 78 is preferably formed of a plastic film. A dimension of the third web 78 in the cross direction CD is preferably slightly smaller than a distance between a pair of lines for folding-back in the cross direction CD.

<Folding Step S3>

In this step, a so-called sailor 81 as a folding guide plate is used to fold back both lateral portions 82, 83 of the first web 71 toward the imaginary center line M along the respective lines R preset for folding-back and the interior surface of the first web folded back and facing itself is previously coated with hot melt adhesive so that the second continuous elastic element 70 and the first continuous elastic element 76 may be interposed and secured between the interior surface of the first web 71 facing itself. The both lateral edges 82, 83 of the first web 71 having been folded back in this manner become closer to each other but preferably these lateral edges 82, 83 are kept out of overlapping with each other. In order that the interior surface of the folded back first web 71 facing itself is reliably joined, it is also possible to guide the first web 71 folded back in this manner to pass through between a pair of nip rollers (not shown).

<First Cutting Step S4>

In this step, the first web 71 having been folded back in the folding step S3 is guided to pass through between a cutter 84 and an anvil roller 85 arranged in a face to face relationship and thereby divided in two to form a pair of fourth webs 87 for the elasticized sheets 43. Consequently, in each of the fourth webs 87, the second continuous elastic element 70 extends along a cut plane 86 formed by the cutter 84 and the first continuous elastic element 76 extending in a region distanced from the second continuous elastic element 70. The fourth web 87 is divided into a joint region 71c formed with gathers owing to existence of the second continuous elastic element 70, an elasticized region 71b in which the first continuous elastic element 76 is present and a non-elasticized region 71a defined between the joint region 71c and the elasticized region 71b and having none of the continuous elastic elements therein.

<Shrinking/Bonding Step S5>

In this step, the fourth web 87 is shrunk between a pair of feed rollers 88 and a pair of circumferential velocity regulating rollers 90 arranged downstream of the feed rollers 88 as viewed in the machine direction M and operating at a circumferential velocity lower than that of the feed rollers 88 and, at the circumferential velocity regulating rollers 90, second webs 91, 92 for the interior sheet 44 and the exterior sheet 45 respectively constituting the base layer 42 are continuously fed so that the fourth webs 87 may be joined to both side edge portions of the respective second webs 91, 92.

A circumferential velocity V1 of the supply rollers 88 is higher than a circumferential velocity V2 of the circumferential velocity regulating rollers 90 and a ratio of the circumferential velocity V1 versus the circumferential velocity V2 (V1/V2 100) is in a range of 105 to 150%, preferably, in a range of 110 to 140%. In other words, the feed rollers 88 rotate at a circumferential velocity of 1.05 to 1.5 times, preferably of 1.1 to 1.4 times of the circumferential velocity V2 of the circumferential velocity regulating rollers 90. The circumferential velocity V1 of the supply rollers 88 and the circumferential velocity V2 of the circumferential velocity regulating rollers 90 may be adjusted to control a dimension ratio of the fourth web 87 before and after contraction thereof and to maintain the respective stretch ratios of the second continuous elastic element 70 and the first continuous elastic element 76 at values larger than 1.

FIG. 7 is a schematic diagram illustrating a state of the fourth web 87 for the elasticized leg sheet 43 being shrunk in the course of the manufacturing process, wherein FIG. 7(a) illustrates the state of the fourth web 87 on the assumption that the second continuous elastic element 70 is not present, and FIG. 7(b) is the schematic diagram illustrating the state of the fourth web 87 on the assumption that the second continuous elastic element 70 is used.

As illustrated in FIG. 7(a), gathers are formed in the elasticized region 71b in which the first continuous elastic elements 70 are joined to the fourth web 87 owing to contraction of the first continuous elastic element 76. In addition, the first continuous elastic element 76 is conveyed under tension and consequently the elasticized region 71b is kept in a horizontal position during conveyance of the fourth web 87. The non-elasticized region 71a of the fourth web 87 in which the continuous elastic element is not present is also stably conveyed without sagging since the third web 78 interposed between a pair of the first web 71 is under tension. However, the non-elasticized region 71a of the fourth web 87 is deformed so as to wave in a vertical direction with respect to the machine direction MD under the influence of contraction of the first continuous elastic elements 76. If it is tried, in such situation, to join the respective fourth webs 87 to the both side edge portions of the second webs 91, 92, the large wavy wrinkles formed in the non-elasticized region 71a will cause a gap to be left after joining since such large wavy wrinkles in the non-elasticized region 71a inevitably reaches a region corresponding to the joint region 71c. Consequently, such gap should not cause leakage of body exudates.

In contrast, when the second continuous elastic element 70 is used as illustrated in FIG. 7(b), fine gathers are formed in the joint region 71c extending along the second continuous elastic element 70 under contraction of the second continuous elastic element 70 having its stretch ratio maintained larger than 1 in the manufacturing process for the diaper 10 and the large wavy wrinkles formed in the non-elasticized region 71a of the fourth web 87 should not reach the joint region 71c. In addition, the second continuous elastic element 70 is under a tension during conveyance of the first web 71 and, in consequence, the joint region 71c extending along the second continuous elastic element 70, i.e., the portion corresponding to the joint region 57c of the elasticized leg sheet 43 is kept in a horizontal position and stably conveyed. In this manner, no significant wrinkle is formed in the joint region 71c when the fourth webs 87 are joined to the both side edge portions of the respective second webs 91, 92, and a possibility that a gap may be left in the joint region 71c and body exudates may leak out through this gap is effectively prevented.

The second webs 91, 92 are fed to the circumferential velocity regulating rollers 90 after the surfaces to be joined to the fourth webs 87 have been coated with hot melt adhesive. The joint regions 71c extending along the second continuous elastic elements 70 of the respective fourth webs 87 in shrunk states are joined to the respective both side edge portions of the second webs 91, 92. In this way, it is possible to join the fourth webs 87 being kept in a shrunk state to the respective both side edge portions of the second webs 91, 92.

In this step, the first webs 71 are joined to the respective both side edge portions of the second webs 91, 92 and whereby a composite web 97 is formed.

<Second Cutting Step S6>

In this step, the composite web 97 is continuously fed to pass through between the cutter 94 and the anvil 94 and cut along the cut line extending in the cross direction CD. Whereby the crotch panel 13 is obtained providing with the base layer 42 having the elasticized leg sheets 43 along the both side edges.

<Assembling Step S7>

In this step, the crotch panel 13 obtained in the second cutting step S6 is conveyed with use of well known conveying technique such as suction conveyance or roller conveyance without affecting the shrunk state of the elasticized leg sheets 43 to the other manufacturing line and joined to the crotch region 16 in a chassis 93 of the diaper 10 manufactured in this line. In a further later step, the absorbent structure 11 (not shown) may be joined to the crotch panel 13 to obtain the diaper 1.

As will be apparent to those skilled in the art from the above description, the base materials are under tension in the manufacturing process for the diaper 10 according to the present invention so that the stretch ratios of the second continuous elastic elements 70 and the first continuous elastic elements 76 before and after contraction may be maintained at values larger than 1. In addition, the stretch ratio of the second continuous elastic elements 70 is maintained at the value larger than 1 so that, in the shrinking/joining step S5, the large wrinkles formed in the non-elasticized region 71a should not reach the joint region 71c extending along the second continuous elastic elements 70. Consequently, large wrinkles should not be formed in the joint region 71c when the four webs 87 are joined to the respective both side edge portions of the second webs 91, 92, and the likelihood that the gap may be left in the joint region 71c after joining and body exudates may leak out from the diaper through this gap is effectively prevented. As further another advantageous effect of the stretch ratio of the first continuous elastic elements 76 maintained at a value larger than 1, the stretch ratio of the first leg elastic elements 50 secured along the leg-openings 23 are also maintained at a value larger than 1 and, with the wearing article put on the wearer's body, the leg-openings 23 sufficiently stretch and contract along the wearer's thighs at a desirable fit. In this way, not only it is possible to prevent body exudates from leaking out of the article but also it is possible to prevent the leg-openings 23 from being tucked down between the wearer's buttocks and partially exposed to the outside.

While the manufacturing process according to the present invention has been described above on the basis of a particular embodiment, the present invention is not limited to this embodiment. For example, it is also possible to, after the first webs 71 have been folded back along the lines R preset for folding-back toward the imaginary center line M, the elasticized regions 71b of the first webs 71 in which the first continuous elastic elements 76 are present (i.e., the regions corresponding to the elasticized regions 57b of the elasticized leg sheets 43) are guided to pass through between a pair of mating toothed rollers for pleating treatment. The elasticized regions 71b may be subjected to the pleating treatment as described above to improve a texture of the leg-openings 23 defined by the elasticized leg sheets 43. Further, the manufacturing process according to the present invention has been described hereinabove on the basis of the embodiment making it possible to obtain a pair of the fourth webs 87 at once from the single first web 71. Certainly, this manufacturing process makes it possible to manufacture, at high efficiency, the wearing article provided with the elasticized leg sheets 43 functioning to keep the leg-openings 23 in close contact with the wearer's body, thereby preventing body exudates from leaking out of the article. However, when the single fourth web 87 is obtained from the single first web 71 and the fourth webs 87 obtained in this manner are joined to the respective both side edge portions of the second webs 91, 92 at once or sequentially is also within the scope of the present invention.

The constituent elements of the disposable diaper 10 are not limited to those described in the specification but the other various types of materials widely used in the relevant technical field may be used without limitation unless otherwise stated. For example, the respective continuous elastic elements may be formed of not only the elastic yarns but also sheet-like elastic material made of urethane resin or the like having given width and thickness. The terms "first", "second", "third" and "fourth" used in the specification and claims of the present invention are not ordinal numbers but used merely to distinguish the similar elements, similar positions or the other similar items.

Embodiments in accordance with the disclosure of the wearing article according to the present invention described hereinabove may be arranged at least as follows:

A wearing article having a longitudinal direction, and a transverse direction, a skin-facing surface and a non-skin-facing surface, and including a front waist region, a rear waist region and a crotch region extending between the front and rear waist regions wherein the front and rear waist regions are joined to each other to form an annular elastic waist panel, a crotch panel is located in the crotch region so as to extend between the front and rear waist regions and an absorbent structure is located in a central area on the skin-facing surface of the crotch panel, wherein a pair of elasticized leg sheets extending in the longitudinal direction are joined to respective side edge portions of a base layer as a constituent of the crotch panel; the elasticized leg sheets respectively include side sheets, a first elastic element and a second elastic element; each of the side sheets has a proximal side edge joined to the base layer and extending in the longitudinal direction and a distal side edge opposition to the proximal side edge and extending in the longitudinal direction and divided into a joint region extending along the proximal side edge, an elasticized region extending along the distal side edge and a non-elasticized region extending between the joint region and the elasticized region and provided with none of elastic elements; the second leg elastic elements are contractibly arranged under tension in the longitudinal direction along the joint region of the elasticized leg sheet and the first leg elastic elements are contractibly arranged under tension in the longitudinal direction in the elasticized region; and each of the elasticized leg sheets is joined to the base layer in such a state that the side sheet is shrunk thereby together with the first leg elastic elements and the second leg elastic elements but a stretch ratio of the first and second leg elastic elements is maintained at a value larger than 1 and a number of gathers extending in parallel in the transverse direction are formed in the joint region.

The present invention disclosed above may include embodiments at least as described below:

(1) The second leg elastic elements are arranged in the joint region.

(2) In the longitudinal direction, a ratio of a dimension of the elasticized leg sheet before contraction versus a dimension thereof after contraction is in a range of 1.05 to 1.5.

(3) The first leg elastic elements are secured to the side sheet at a stretch ratio higher than that of the second leg elastic elements.

(4) The elasticized leg sheet further includes a reinforcing sheet adapted to cover the first leg elastic elements and the second leg elastic elements.

(5) The elasticized region of the elasticized leg sheet is subjected to a pleating treatment.

Embodiments in accordance with the disclosure of the manufacturing process for the wearing article according to the present invention described above may be arranged at least as follows:

A manufacturing process for the wearing article according to claim 1 including the steps of: continuously feeding a first continuous elastic element and a second continuous elastic element in a machine direction and contractibly securing under tension and to a first web for the side sheet, then folding back the first web along a line preset for folding-back, joining the interior surface of the first web having been folded back so as to face itself and to interpose the first and second continuous elastic elements therebetween in a manner that the first continuous elastic element is arranged along the line preset for holding-back and the second continuous elastic element is arranged at a distance from the first continuous elastic element; shrinking the first web having been folded back in the machine direction so that respective stretch ratios of the first and second continuous elastic elements after having been shrunk are maintained at a value larger than 1; continuously feeding second webs for abase layer in the crotch panel in the machine direction and joining a joint region extending along the second continuous elastic element in the first web still being maintained in a shrunk state to the respective both side edge portions of the second web at once or sequentially; cutting a composite web composed of the first web joined to the both side edge portions of the second web in a direction orthogonal to the machine direction; and joining respective pieces of the composite web obtained in the step of cutting the composite web to a crotch region in a chassis manufactured in a separate manufacturing line and having the front waist region, the rear waist region and the crotch region extending between the front and rear waist regions.

The present invention disclosed just above may include embodiments at least as described below:

(1) The process further including a step of covering the first and second continuous elastic elements with a third web prior to the step of folding back the first web.

(2) In the step of shrinking the first web folded back, a dimension ratio of the first web before and after contraction in the longitudinal direction is in a range of 1.05 to 1.5.

(3) A pair of the first continuous elastic elements and a pair of the second continuous elastic elements are supplied symmetrically about an imaginary center line bisecting a dimension of the first web in a direction orthogonal to the machine direction; a pair of the second continuous elastic elements are secured to the first web symmetrically about the imaginary center line so as to be adjacent to the imaginary center line; a pair of the first continuous elastic elements are secured to the first web between respective lines preset for folding-back defined between the imaginary center line and the respective side edges of the first web and extending in the machine direction and the imaginary center line so as to be distanced from the respective second continuous elastic elements; and, in the step of folding back the first web, the both side edge portions of the first web along the lines preset for folding-back toward the imaginary center line, and the first and second continuous elastic elements are interposed between the folded back first web, then the first web is cut in half along the imaginary center line, the respective halves of the first web each including the first and second continuous elastic elements are distanced from each other in a direction orthogonal to the machine direction, then the respective halves of the first web are shrunk at the same contraction ratio and thereafter joined to the both side edge portions of the second web.

(4) The second continuous elastic element is arranged in the joint region and extends in the machine direction.

(5) The manufacturing process further including a step of, after the first web has been folded back, subjecting an elasticized region of the first web in which the first continuous elastic element is present to a pleating treatment.

REFERENCE SIGNS LIST 10 wearing article (disposable diaper)
11 absorbent structure
12 elastic waist panel
13 crotch panel
14 front waist region
15 rear waist region
16 crotch region
42 base layer
43 elasticized leg sheet
43c distal side edge
43d proximal side edge
50 first leg elastic elements
51 side sheet
52 reinforcing sheet
57a non-elasticized region
57b elasticized region
57c joint region
61 second leg-elastic elements
70 second continuous elastic element
71 first web
71a non-elasticized region
71b elasticized region
71c joint region
76 first continuous elastic element
91 second web
92 second web
97 composite web
X transverse direction
Y longitudinal direction
MD machine direction
R line preset for folding-back

The invention claimed is:

1. A wearing article having a longitudinal direction, and a transverse direction, a skin-facing surface and a non-skin-facing surface, said wearing article comprising:
a front waist region, a rear waist region and a crotch region extending between the front and rear waist regions, wherein the front and rear waist regions are joined to each other to form an annular elastic waist panel,
a crotch panel located in the crotch region and extending between the front and rear waist regions,
an absorbent structure located in a central area on the skin-facing surface of the crotch panel,
wherein
the crotch panel includes
a base layer, and
a pair of elasticized leg sheets extending in the longitudinal direction and joined to respective side edge portions of the base layer,
the elasticized leg sheets each respectively include a side sheet, a first leg elastic element, and a second leg elastic element,
in each of the elasticized leg sheets, the side sheet has
a proximal side edge joined to the base layer and extending in the longitudinal direction, and
a distal side edge facing the proximal side edge and extending in the longitudinal direction and being divided into
a joint region extending along the proximal side edge,
an elasticized region extending along the distal side edge, and
a non-elasticized region extending between the joint region and the elasticized region and provided with no elastic elements,
the second leg elastic element is contractibly arranged under tension in the longitudinal direction along the joint region,
the first leg elastic element is contractibly arranged under tension in the longitudinal direction in the elasticized region,
the first leg elastic elements are disposed at the distal side edges of the side sheets defining lateral side edges of the crotch panel opposite to each other in the transverse direction,
each of the elasticized leg sheets is joined to the base layer in such a state that the side sheet is shrunk together with the first leg elastic element and the second leg elastic element but a stretch ratio of the first and second leg elastic elements is maintained at a value larger than 1 and a number of gathers extending in parallel in the transverse direction are formed in the joint region, and
the first leg elastic elements are secured to the side sheets at a stretch ratio higher than that of the second leg elastic elements.

2. The wearing article according to claim 1, wherein the second leg elastic elements are arranged in the joint regions.

3. The wearing article according to claim 1, wherein, in the longitudinal direction, a ratio of a dimension of each of the elasticized leg sheets before contraction versus a dimension thereof after contraction is in a range of 1.05 to 1.5.

4. The wearing article according to claim 1, wherein each of the elasticized leg sheets further includes a reinforcing sheet covering the corresponding first leg elastic element and the corresponding second leg elastic element.

5. The wearing article according to claim 1, wherein the elasticized region of each of the elasticized leg sheets includes pleats.

6. The wearing article according to claim 1, wherein in each of the elasticized leg sheets, the second leg elastic element is disposed in the joint region and inward of the first leg elastic element in the transverse direction.

7. A process for manufacturing a wearing article having a longitudinal direction and a transverse direction, a skin-facing surface and a non-skin-facing surface, and said wearing article further including a front waist region, a rear waist region and a crotch region extending between the front and rear waist regions,
wherein
the front and rear waist regions are joined to each other to form an annular elastic waist panel,
a crotch panel is located in the crotch region so as to extend between the front and rear waist regions and an absorbent structure is located in a central area on the skin-facing surface of the crotch panel, a pair of elasticized leg sheets extending in the longitudinal direction are joined to respective side edge portions of a base layer as a constituent of the crotch panel, the elasticized leg sheets respectively include side sheets, a first leg elastic element, and a second leg elastic element, each of the side sheets has a proximal side edge joined to the base layer and extending in the longitudinal direction, and a distal side edge facing the proximal side edge and extending in the longitudinal direction and being divided into a joint region extending along the proximal side edge, an elasticized region extending along the distal side edge, and a non-elasticized region extending between the joint region and the elasticized region and provided with none of elastic elements, the second leg elastic elements are contractibly arranged under tension in the longitudinal direction along the joint region of the elasticized leg sheet, the first leg elastic elements are contractibly arranged under tension in the longitudinal direction in the elasticized region, and each of the elasticized leg sheets is joined to the base layer in such a state that the side sheet is shrunk together with the first leg elastic elements and the second leg elastic elements but a stretch ratio of the first and second leg elastic elements is maintained at a value larger than 1 and a number of gathers extending in parallel in the transverse direction are formed in the joint region, said method comprising the steps of:

continuously feeding first and second continuous elastic elements for the first and second leg elastic elements in a machine direction and contractibly securing under tension to a first web for the side sheet, then folding back the first web along a line preset for folding-back, joining an interior surface of the first web having been folded back so as to face itself and to interpose the first and second continuous elastic elements therebetween in a manner that the first continuous elastic element is arranged along the line preset for folding-back and the second continuous elastic element is arranged at a distance from the first continuous elastic element;

shrinking the first web having been folded back in the machine direction so that respective stretch ratios of the first and second continuous elastic elements after having been shrunk are maintained at a value larger than 1;

continuously feeding a second web for the base layer in the crotch panel in the machine direction and bonding a joint region of the first web, extending along the second continuous elastic element in the first web still being maintained in a shrunk state, to respective both side edge portions of the second web at once or sequentially;

cutting a composite web composed of the first web joined to the both side edge portions of the second web in a direction orthogonal to the machine direction; and joining respective pieces of the composite web obtained in the step of cutting the composite web to a crotch region in a chassis manufactured in a separate manufacturing line and having the front waist region, the rear waist region and the crotch region extending between the front and rear waist regions.

8. The process according to claim 7, further comprising a step of covering the first and second continuous elastic elements with a third web prior to the step of folding back the first web.

9. The process according to claim 7, wherein, in the step of shrinking the first web, a dimension ratio of the first web before and after contraction in the machine direction is in a range of 1.05 to 1.5.

10. The process according to claim 7, wherein a pair of the first continuous elastic elements and a pair of the second continuous elastic elements are supplied symmetrically about an imaginary center line bisecting a dimension of the first web in the direction orthogonal to the machine direction, the pair of the second continuous elastic elements are secured to the first web symmetrically about the imaginary center line so as to be adjacent to the imaginary center line, the pair of the first continuous elastic elements are secured to the first web between respective lines preset for folding-back defined between the imaginary center line and the respective side edges of the first web and extending in the machine direction and the imaginary center line so as to be distanced from the respective second continuous elastic elements, and in the step of folding back the first web, both side edge portions of the first web are folded along the lines preset for folding-back toward the imaginary center line to interpose the first and second continuous elastic elements therebetween, then the folded back first web is cut in half along the imaginary center line, the respective halves of the first web each including the first and second continuous elastic elements are distanced from each other in the direction orthogonal to the machine direction, then the respective halves of the first web are shrunk at a same contraction ratio and thereafter joined to the both side edge portions of the second web.

11. The process according to claim 7, wherein the second continuous elastic element is arranged in the joint region of the first web and extends in the machine direction.

12. The process according to claim 7, further comprising a step of, after the first web has been folded back, subjecting an elasticized region of the first web in which the first continuous elastic element is present to a pleating treatment.

* * * * *